United States Patent [19]

Frey et al.

[11] Patent Number: 5,672,772
[45] Date of Patent: Sep. 30, 1997

[54] PROCESS FOR REMOVAL OF NITRILES FROM ETHERIFICATION FEEDSTOCKS

[75] Inventors: Stanley J. Frey, Palatine; Paul R. Cottrell, Arlington Heights; David A. Hamm, Hinsdale, all of Ill.

[73] Assignee: UOP, Des Plaines, Ill.

[21] Appl. No.: 630,288

[22] Filed: Apr. 10, 1996

Related U.S. Application Data

[63] Continuation-in-part of Ser. No. 237,532, May 3, 1994, Pat. No. 5,569,790.
[51] Int. Cl.$^6$ .................................................. C07C 41/00
[52] U.S. Cl. .................................................. 568/699
[58] Field of Search .................................................. 568/699

[56] References Cited

U.S. PATENT DOCUMENTS

| | | | |
|---|---|---|---|
| 2,720,547 | 10/1955 | Wolf et al. | 260/614 |
| 4,219,678 | 8/1980 | Obenaus et al. | 568/697 |
| 5,271,835 | 12/1993 | Gorawara et al. | 208/228 |

FOREIGN PATENT DOCUMENTS 2063019  9/1993  Canada.

OTHER PUBLICATIONS

Stinson, Stephen C., "New plants, processes set for octane booster", Chemical and Engineering News, Jun. 25, 1979 edition, p. 35.

*Primary Examiner*—Paul J. Killos
*Attorney, Agent, or Firm*—Thomas K. McBride; John G. Tolomei; Richard P. Silverman

[57] ABSTRACT

A process is disclosed for improving catalyst performance and yields in the manufacture of motor gasoline components. More particularly the process is directed to the removal of trace amounts of acetonitrile or acetone or propionitrile from a hydrocarbon feedstock such as a $C_4$–$C_6$ product fraction from a fluid catalytic cracking unit, which may be used subsequently in an etherification process for the production of ethers such as MTBE and TAME. The hydrocarbon feedstock is passed to a water wash zone for the removal of the trace amounts of acetonitrile or acetone or propionitrile and the spent water comprising the nitriles is contacted with a nitrile-lean stream to regenerate the wash water. A portion of the spent water stream is withdrawn to reduce the nitrile level in the nitrile-lean water stream. The combined water wash, regeneration, and water recycle steps provide protection for the etherification zone catalyst with a significantly reduced requirement for wash water and spent wash water disposal.

18 Claims, 3 Drawing Sheets

PROCESS FOR REMOVAL OF NITRILES FROM ETHERIFICATION FEEDSTOCKS

CROSS-REFERENCE TO RELATED APPLICATIONS

This application is a continuation-in-part of application No. 08/237,532, filed May 3, 1994, now U.S. Pat. No. 5,569,790, and is hereby incorporated by reference.

FIELD OF THE INVENTION

This invention relates to a process for the removal of trace polar compounds and specifically acetonitrile, propionitrile, and acetone from a feedstream to an etherification reaction zone derived from a feedstock containing $C_3$–$C_5$ hydrocarbons comprising olefins and paraffins.

DISCUSSION OF RELATED ART

Etherification processes are currently in great demand for making high octane compounds which are used as blending components in lead-free gasoline. These etherification processes will usually produce ethers by combination of an isoolefin with a monohydroxy alcohol such as methanol or ethanol. The etherification process can also be used as a means to produce pure isoolefins by cracking of the product ether. For instance, pure isobutylene can be obtained for the manufacture of polyisobutylenes and tert-butyl-phenol by cracking methyl tertiary butyl ether (MTBE). The production of MTBE has emerged as a predominant etherification process which uses $C_4$ isoolefins as the feedstock. A detailed description of processes, including catalyst, processing conditions, and product recovery, for the production of MTBE from isobutylene and methanol are provided in U.S. Pat. Nos. 2,720,547 and 4,219,678 and in an article at page 35 of the Jun. 25, 1979 edition of Chemical and Engineering News. The preferred process is described in a paper presented at The American Institute of Chemical Engineers, 85th National Meeting on Jun. 4–8, 1978, by F. Obenaus et al. The above references are herein incorporated by reference. Other etherification processes of current interest are the production of tertiary amyl methyl ether (TAME) by reacting $C_5$ isoolefins with methanol, and the production of ethyl tertiary butyl ether (ETBE) by reacting $C_4$ isoolefins with ethanol, the production of tertiary amyl ethyl ether (TAEE) by reacting $C_5$ isoolefins with ethanol, and the production of tertiary hexyl methyl ether (THME) by reacting $C_6$ isoolefins with methanol.

The fluid catalytic cracking (FCC) process is a process for the conversion of straight-run atmospheric gas oil, vacuum gas oils, certain atmospheric residues, and heavy stocks recovered from other operations into high-octane gasoline, light fuel oils, and olefin-rich light gases. In a petroleum refinery the FCC unit typically processes 30 to 50% of the crude oil charged to the refinery. Early FCC units were designed to operate on vacuum gas oils directly fractionated from crude oils. Typically, these vacuum gas oils came from high quality crude oils. Today, much of the high quality feedstock for FCC units has been depleted and modern FCC units process less favorable materials. These less favorable materials include a substantial amount of sulfur containing materials and a growing portion of the non-distillable fraction of the crude oil. As a result, the contaminant level of the FCC product fractions have increased, particularly in the $C_3$–$C_5$ product fraction. Without appropriate treatment, the contaminants in the $C_3$–$C_5$ product fractions can be transmitted to sensitive downstream processes where they reduce the effectiveness of downstream catalysts and create unfavorable by-product reactions in processes such as alkylation and etherification.

Propylene, butylene and pentenes make up the majority of the olefin-rich light products produced in the catalytic cracking of crude oil. Propylene is typically used with propane as a fuel. Propylene is also used as a feedstock in the manufacture of iso-propanol, acrylonitrile, propylene oxide, and polypropylene. As such, propylene must meet "chemical grade" or "polymer grade" purity specifications and meet a corrosive sulfur specification, respectively. Essentially all of the butylene and the major fraction of the propylene may be subsequently alkylated with iso-butane or etherified with methanol to produce motor gasoline. Pentenes, which are obtained by depentanizing of FCC gasoline, are often present in the olefin feed to the alkylation unit and alkylated with isobutane. Pentenes may also be used in the production of TAME, tertiary amyl methyl ether, an oxygenate used in the production of oxygen containing gasoline and reformulated gasoline.

In a number of refineries which operate the FCC at high severities on heavy, high-sulfur crudes, a combination of amine treating and mercaptan sulfur removal has not been sufficient to overcome a the premature loss of catalyst life in etherification processes resulting from the presence of nitriles in the feedstream to the etherification process. When water is present in the feedstream along with the nitriles, the nitriles undergo a hydrolysis reaction over the etherification catalyst forming ammonia. This ammonia subsequently causes the premature deactivation of the etherification catalyst.

U.S. Pat. No. 5,271,835 to Gorawara et al. discloses a combination of processes to remove sulfur compounds and trace polar compounds including nitriles such as acetonitrile and propionitrile from a light olefin feedstream derived from an FCC process with an integrated combination of scrubbing with an alkanolamine, mercaptan sulfur removal, and an adsorption zone.

Other schemes for the removal of nitriles from etherification feedstreams comprise passing the olefin feedstream to a selective hydrogenation process to remove sulfur and convert any mercaptan sulfur to monosulfides. The hydrogenated feedstream is then passed to a once-through water wash column to remove the trace amounts of nitriles. For example, to remove acetonitrile from the hydrogenated olefin feedstream, a water wash in an amount equivalent to about 20% of the feedstream is required. Based on the reduced solubility of propionitrile in water, to reduce the concentration of propionitrile in the olefin feedstream to less than 5 ppm-wt, the once-through water wash rates typically can mount to up to 50% and often exceed about 100% of the olefin feedstream rate. In once-through fresh water systems, the fresh water, or makeup water is typically treated to remove metal cations such as $Ca^{+2}$, $Na^+$, $K^+$, $Fe^{+2}$, and $Mg^{+2}$ which may enter the hydrocarbon stream and deactivate the etherification unit catalyst. In addition, the spent wash water must be sent to a safe disposal system to remove the hydrocarbons and nitriles to comply with environmental regulations. Typical treatment in a petroleum refinery includes sending the spent wash water to a sour water stripping operation.

Processes are sought which minimize the spent water disposal problems of the conventional schemes and avoid the high cost of adsorbent based system.

BRIEF SUMMARY OF THE INVENTION

It is a broad object of this invention to provide an effective means for improving catalyst life, enhancing yields and improving the economic benefits of producing motor gasoline components in etherification units. Often the feedstream to the etherification unit can contain trace amounts of polar compounds, specifically oxygenates and nitrogen compounds, and more specifically those oxygenates and nitrogen compounds comprising alcohols, ketones and nitriles having 1 to 3 carbon numbers, and most specifically, acetone or acetonitrile or propionitrile. This invention provides a simple and highly effective means for their removal. By the process of the present invention, a wash water step prior to the etherification reactor may operate at a water rate necessary to remove essentially all of the nitriles without producing a large amount of spent waste water. In fact, by the recontacting of the spent wash water with a hydrocarbon stream such as the unconverted $C_4$–$C_6$ hydrocarbons according to the present invention, the wash water makeup rate is significantly less than the once-through water rate. The invention may be employed in process arrangements that convert the $C_4$–$C_6$ product fraction from an FCC into alkylate or into ethers to produce high octane motor gasoline blending components for reformulated gasolines. This invention improves the operation of downstream alkylation and etherification processes toward the production of reformulated gasoline.

The invention provides a process for the removal of nitriles including acetonitrile, propionitrile and mixtures thereof from a feedstream comprising $C_4$–$C_6$ hydrocarbons to an etherification zone. The process comprises passing the feedstream at water wash conditions including a water wash temperature to a water wash zone. In the water wash zone, the feedstream is contacted with a regenerated water stream to provide a hydrocarbon feedstream depleted in the nitriles and a spent water stream. The spent water stream is enriched in nitriles relative to the regenerated water stream. At least a portion of the spent water stream at water regenerator conditions including a water regeneration temperature is passed to a water regeneration zone. In the water regeneration zone, the spent water stream is contacted with a nitrile-lean stream to absorb at least a portion of the nitriles from the spent water stream and to provide a nitrile-rich raffinate stream and a nitrile-lean water stream. At least a portion of the nitrile-lean water stream is admixed with a make up water stream to provide the regenerated water stream for the water wash zone.

In one embodiment, the invention is an etherification process comprising passing a feedstream including $C_4$–$C_6$ hydrocarbons and nitriles to a water wash zone. In the water wash zone the feedstream is contacted with a regenerated water stream to absorb the nitriles and to provide a hydrocarbon feedstream depleted in the nitriles and a spent water stream. The spent water stream is enriched in the nitriles relative to the regenerated water stream. The hydrocarbon feedstream is admixed with an alcohol stream to provide a reaction mixture. The reaction mixture is passed to an etherification zone to provide a reaction product comprising an ether and unreacted $C_4$–$C_6$ hydrocarbons. The reaction product from the reaction zone is separated in a distillation zone. The distillation zone contains at least a portion of the reaction zone. The distillation zone provides an overhead stream comprising unreacted alcohol and unreacted $C_4$–$C_6$ hydrocarbons and a bottoms stream comprising the ether. The overhead stream is passed to a raffinate wash zone wherein the overhead stream is contacted with a raffinate wash water stream to absorb at least a portion of the unreacted alcohol into a raffinate waste water stream and to provide a raffinate stream essentially free of the alcohol comprising the unreacted $C_4$–$C_6$ hydrocarbons. The raffinate stream is passed to a water regeneration zone. In the water regeneration zone, the raffinate stream is contacted with at least a portion of the spent water stream to desorb at least a portion of the nitriles from the spent water stream and to provide a nitrile enriched raffinate stream and a nitrile-lean water stream. At least a portion of the nitrile-lean water stream is admixed with a make up water stream to provide the regenerated water stream.

Additional embodiments, aspects and details of this invention are set forth in the following detailed description.

DETAILED DESCRIPTION OF THE INVENTION

Figure 1:
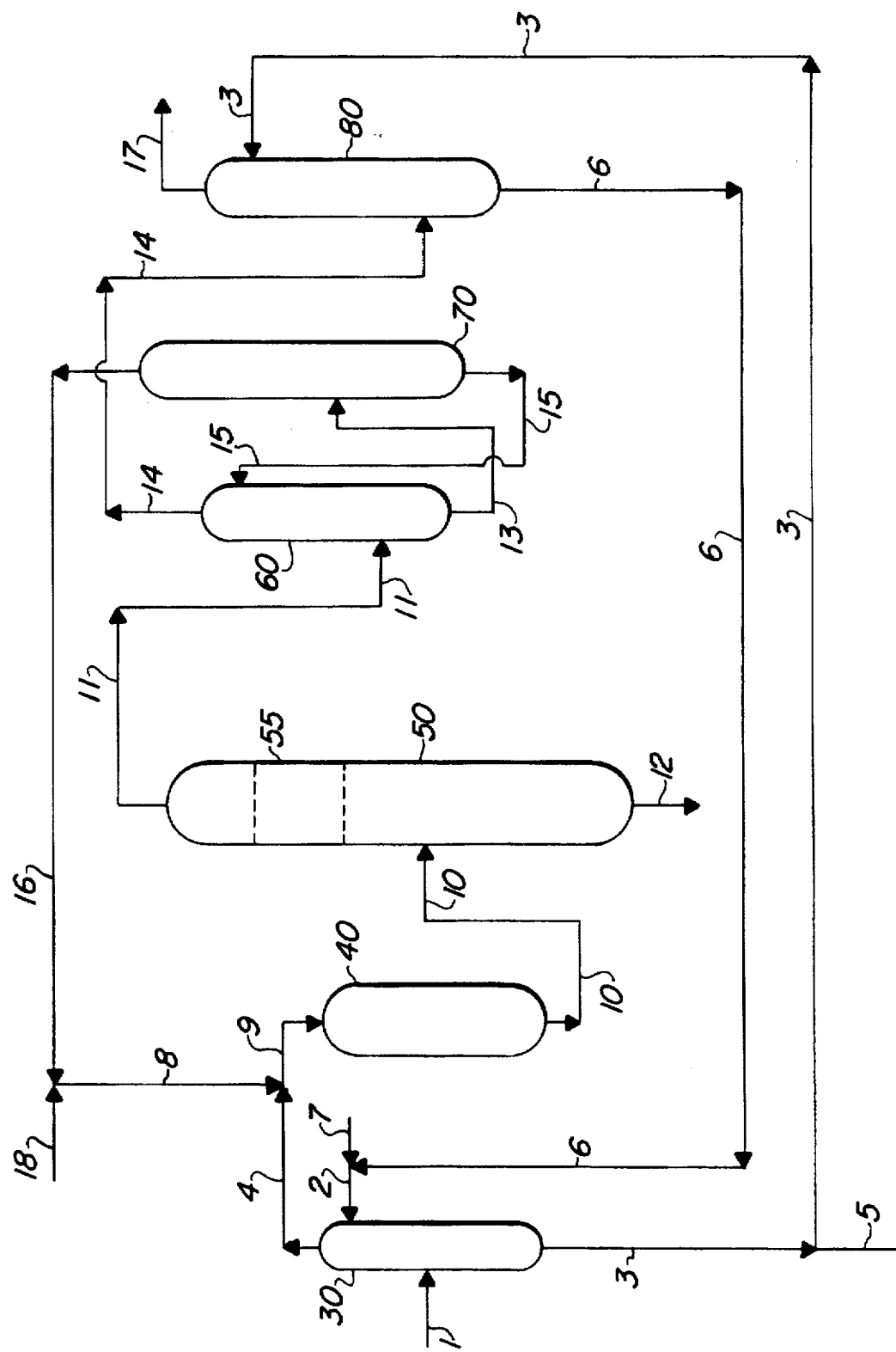
FIG. 1 is a schematic illustration of the process for the removal of nitrile from a feedstream according to the process of the instant invention.

The hydrocarbon feedstream being treated in accordance with this invention may be derived from a fluid catalytic cracking (FCC) unit and typically is composed of any proportion of monoolefin and paraffin, each containing from 3 to 6 carbon atoms, but preferably is comprised of a major proportion of paraffin with respect to the monoolefin constituent. The paraffin include isobutane, isopentane, normal pentane, as well as propane and n-butane. The monoolefins include butene-1, butene-2, isobutene, 2-methyl-2-butene, 2-methyl-1-butene, 3-methyl-1-butene, 1-pentane, 2-pentane, cyclopentene and propylene. The hydrocarbon feedstream may also contain diolefins such as 1,3-butadiene and 1,3-pentadiene. Minor proportions of both paraffinic and olefinic molecules of various numbers of carbon atoms which can result from distillation procedures to obtain the $C_4$–$C_6$ hydrocarbons are not harmful to the process and can be present. The hydrocarbon feedstream typically contains 30 to 60 mol % olefins.

Nitrogen compounds, particularly acetonitrile, are present in the hydrocarbon feedstream in trace amounts ranging from about 10 to about 500 ppm-wt and more typically from about 15 to about 80 ppm-wt. The term nitriles as used herein refers to nitrogen-containing compounds such as acetonitrile, propionitrile, and mixtures thereof. Other nitrile compounds such as propionitrile also may be present in similar amounts. Water and its precursors may also be present in the hydrocarbon feedstream in amounts from 5 ppm-wt to saturation which typically is about 500 ppm-wt, measured as $H_2O$. The contaminants may also include oxygenated hydrocarbon compounds, otherwise known as oxygenates, such as alcohols, ethers, aldehydes, ketones, and acids. Specific examples of these oxygenates are ethanol, methanol, isopropanol, tertiary butyl alcohol, dimethyl ether, methyl tertiary butyl ether, acetone, and acetic acid. Acetone may be present in trace amounts ranging from about 1 to about 500 wt. ppm. The feedstream may or may not have been subject to a selective hydrogenation process for the saturation of diolefins prior to its use in the pretreating process of the instant invention. Typically, the feedstream from the FCC may contain from about 1000 ppm-wt. to about 2 vol. % butadiene or diolefin. The effluent from a selective hydrogenation process will typically contain less than 50 ppm-wt. diolefins.

A wide variety of catalyst materials has been found to promote the etherification reaction including ion-exchange resins such as divinylbenzene cross-linked polystyrene ion exchange resins in which the active sites are sulfuric acid groups; and inorganic heterogeneous catalysts such as boric acid, bismuth molybdate, and metal salts of phosphomolybdic acids wherein the metal is lead, antimony, tin, iron, cerium, nickel, cobalt or thorium. Also boron phosphate, blue tungsten oxide and crystalline aluminosilicates of the zeolitic molecular sieve type have also been proposed as heterogeneous catalysts for the reaction of methanol or ethanol and isobutylene or isobutylene.

The etherification reaction conditions are not narrowly critical and depend in large part upon the particular catalyst composition employed. Thus, both vapor phase and liquid phase processes have been proposed in which reaction temperatures are from about 50° C. to about 4000° C., reaction pressures vary from about atmospheric to about 1.04 MPa (1500 psig) and stoichiometric molar ratios of alcohol to isoalkene range from 0.2:1 to about 10:1 and preferably, according to a near stoichiometric molar ratio ranging from about 0.95 to about 1.15. Thus, the present process may employ a near stoichiometric ratio of the alcohol with respect to the isoalkene. Both batch type and continuous process schemes may be suitably employed. In the present process the reaction can be carried out in either the vapor phase or the liquid phase, but the liquid phase is preferred. For reaction zone portions within distillation zones, the reaction proceeds primarily in the liquid phase. Isobutylene and isoamylene are the preferred isoalkenes. Methanol is the preferred alcohol, although ethanol may also be employed.

DETAILED DESCRIPTION OF THE DRAWINGS

The further description of the process of this invention is presented with reference to the attached FIG. 1. The FIG. 1 represents the preferred arrangement of the invention and is not intended to be a limitation on the generally broad scope of the invention as set forth in the claims. Of necessity, some miscellaneous appurtenances including valves, pumps, separators, heat exchangers, reboilers, etc. have been eliminated. Only those vessels and lines necessary for a complete and clear understanding of the process of the present invention are illustrated.

Referring to FIG. 1, a feedstream comprising $C_4$–$C_6$ hydrocarbons and nitriles including acetonitrile, propionitrile and mixtures thereof is passed via line 1 to water wash column 30. Preferably, the feedstream comprises about 10 ppm-wt. to about 500 ppm-wt. nitriles. In the water wash column 30, the feedstream is contacted at water washing conditions including a water wash temperature ranging from about 20° C. to about 300° C., and preferably ranging from about 10° C. to about 65° C., with a regenerated water stream in line 2 to provide a hydrocarbon feedstream depleted in the nitriles in line 4 and a spent water stream enriched in the nitriles relative to the regenerated water stream in line 3. Preferably, the hydrocarbon feedstream depleted in the nitriles will comprise from about 0.1 ppm-wt to about 50 ppm-wt nitriles, and more preferably, the hydrocarbon feedstream depleted in nitriles will comprise less than about 25 ppm-wt nitriles and most preferably will contain less than 2 ppm-wt acetonitrile and less than 20 ppm-wt propionitrile. Preferably, the regenerated water stream will contain less than 40 ppm-wt nitriles. At least a portion of the spent water stream in line 3 will be passed to a water regeneration column 80 for the regeneration of the regenerated water. In the water regenerator column 80, the spent water stream 3 is contacted with a raffinate stream 14 comprising unreacted hydrocarbons withdrawn from an etherification zone. Within the water regeneration column 80 at least a portion of the nitriles from the spent water stream are absorbed to provide a nitrile-rich raffinate stream which is withdrawn in line 17 and a nitrile-lean water stream in line 6. At least a portion of the nitrile-lean water stream in line 6 is admixed with a make up water stream in line 7 to provide the regenerated water in line 2 which is subsequently passed to the water wash column. Preferably, the nitrile-lean water stream 6 will contain less than 40 ppm-wt nitriles and, most preferably, contain less than 20 ppm-wt nitriles. The nitrile-rich raffinate stream withdrawn in line 17 may be subsequently passed to a gasoline blending operation where the presence of nitriles in the stream is not critical to the gasoline product quality. As an alternative, a portion of any of the gasoline blending streams such as $C_7$–$C_8$ alkylate, $C_5$–$C_7$ isomerate, polymer gasoline and mixtures thereof may be employed to absorb the nitriles from the spent water stream. In order to keep basic nitrogen compounds and metals from building up in the spent water stream 3 and reduce the nitrile level in the nitrile-lean water stream 6, at least a portion of the spent water stream is withdrawn in line 5 and passed to further effluent treatment, not shown. The water regeneration temperature in column 80 will range from about 20° C. to about 300° C., and preferably will range from about 35° C. to about 95° C. Preferably, the water regenerator column will be operated at conditions less favorable for nitrile solubility in water so that the nitrile partition coefficient of nitrile concentration in the water over nitrile concentration in hydrocarbon is lower in the water regenerator than in the water wash column. It was surprisingly discovered that the lower the propionitrile concentration in the feedstream, the greater the benefits of the present invention in reducing the water wash rate relative to the feedstream rate.

The hydrocarbon feedstream depleted in the nitriles is passed via line 4 and subsequently admixed with an alcohol stream in line 8 to provide a reaction mixture in line 9. The reaction mixture 9 is passed to an etherification zone 40. In the etherification zone the reaction mixture is passed over a resin catalyst at etherification conditions to produce a reaction product comprising an ether and unreacted $C_4$–$C_6$ hydrocarbons. In some embodiments, a single reactor such as 40 is sufficient to provide the necessary conversion to the ether product. Preferably, the reaction product from reaction zone 40 is passed via line 10 to a distillation zone 50 which incorporates an additional reaction zone 55. Distillation zone 50 further facilitates the conversion and separation to provide a bottoms stream, or etherification product stream in line 12 and an overhead stream in line 11 comprising unreacted $C_4$–$C_6$ hydrocarbons and unreacted alcohol. The overhead stream in line 11 is passed to a raffinate wash column 60 where it is contacted with a raffinate wash water stream in line 15 to absorb at least a portion of the unreacted alcohol, and produce a raffinate stream comprising the unreacted $C_4$–$C_6$ hydrocarbons depleted in the alcohol in line 14 and a raffinate waste water stream in line 13. Preferably, the raffinate stream will comprise less than about 20 wt-% unreacted alcohol. The raffinate waste water stream 13 comprising the unreacted alcohol is passed to an alcohol recovery column 70 wherein the unreacted alcohol is separated from the spent raffinate wash water to provide a regenerated raffinate wash water in line 15 and a recycle alcohol stream in line 16. The recycle alcohol stream of line 16 may be combined with a make up alcohol stream in line 18 to provide the alcohol stream in line 8. The raffinate stream in line 14 is passed to the water regeneration column 80 wherein it is countercurrently contacted with the spent wash water stream 3 as described herein above.

Figure 2:
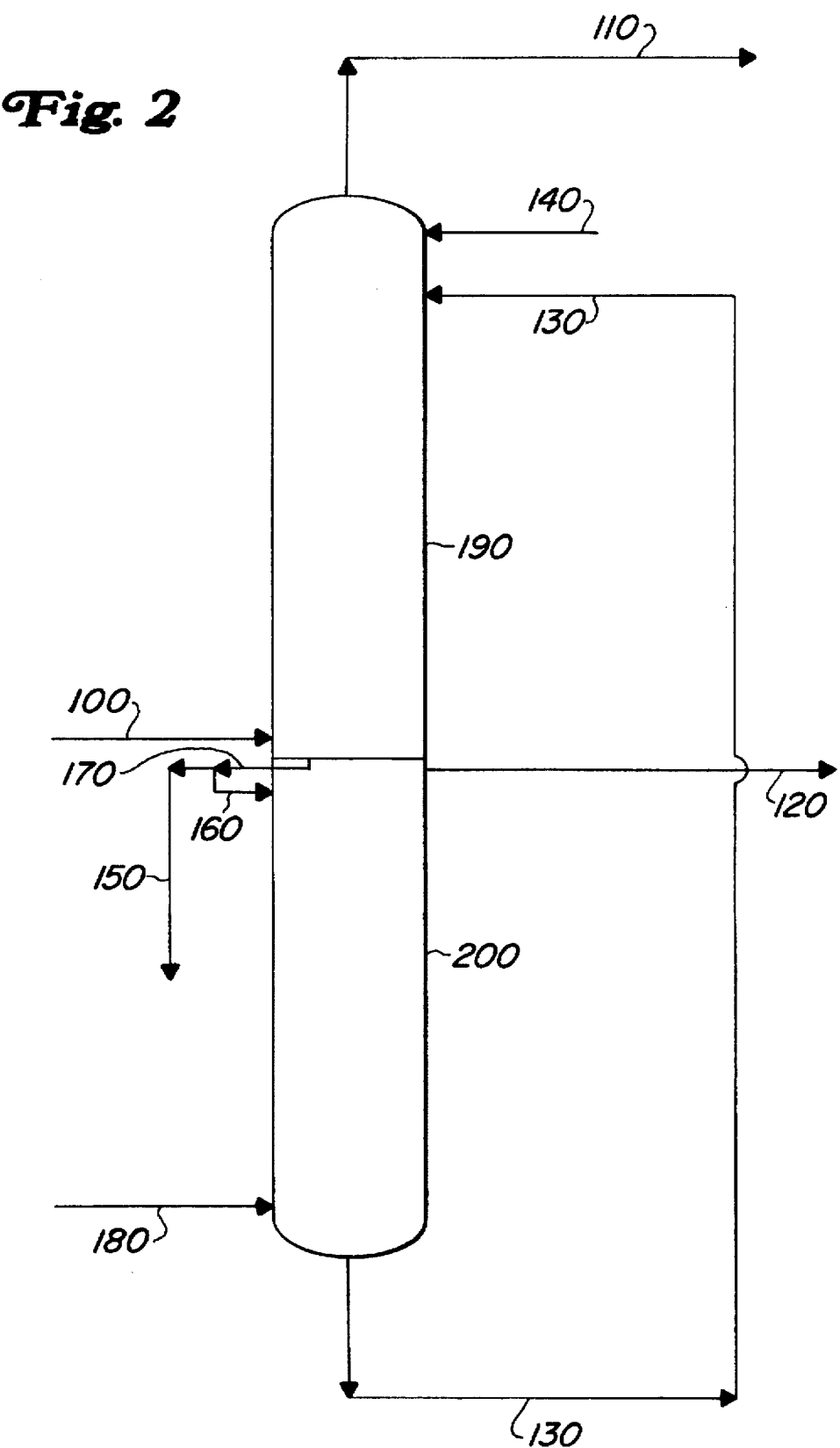
FIG. 2 is a schematic flow diagram of a single column having a wash water zone and a water regeneration zone according to the process of the instant invention.

In a further embodiment, the water wash zone may be combined with the water regenerator zone into a single column having an upper section containing water wash zone 190 and a lower section containing a water regeneration zone 200 as shown in FIG. 2. The feedstream 100 is introduced at a feed point in a lower portion of the water wash zone 190. A regenerated water stream 130 is introduced to the wash water zone 190 at a point in an upper portion of the water wash zone. A make up water stream 140 may be admixed with the nitrile-lean regenerated water stream 130. Preferably, the make up water stream 140 may be introduced to the water wash zone 190 at a point 1–5 trays above the point where stream 130 is introduced to provide a few extra stages of contact between the nitrile-free make up water stream and the regenerated water stream in line 130. A hydrocarbon feedstream depleted in nitriles is withdrawn in line 110. A nitrile-enriched spent water stream 170 is withdrawn from the lower portion of the water wash zone 190 and passed by line 170 and 160 to an upper portion of the water regeneration zone 200. At least a portion of the spent water stream is withdrawn in line 150 for further effluent treatment (not shown). In practice, the spent water stream may flow from the upper water wash zone 190 to the lower water regeneration zone 200 through a downcomer or similar liquid collection device. The portion of the spent water 150 withdrawn from the water wash zone will be withdrawn from the liquid collection device. A nitrile-lean hydrocarbon stream 180, such as etherification raffinate, $C_7$–$C_8$ alkylate or $C_5$–$C_7$ isomerate, is passed to a lower portion of the water regeneration zone 200 and a nitrile-enriched hydrocarbon stream is withdrawn from the top of the water regeneration zone in line 120. The nitrile-lean regenerated water stream 130 is withdrawn from the bottom of the water regeneration zone 200 and passed to the point in the upper portion of the water wash zone 190 as hereinabove described.

The invention will be more fully understood by reference to the following examples, and comparative data which demonstrate the high selectivity for polar compounds of the adsorbent of this invention.

EXAMPLE 1

Figure 3:
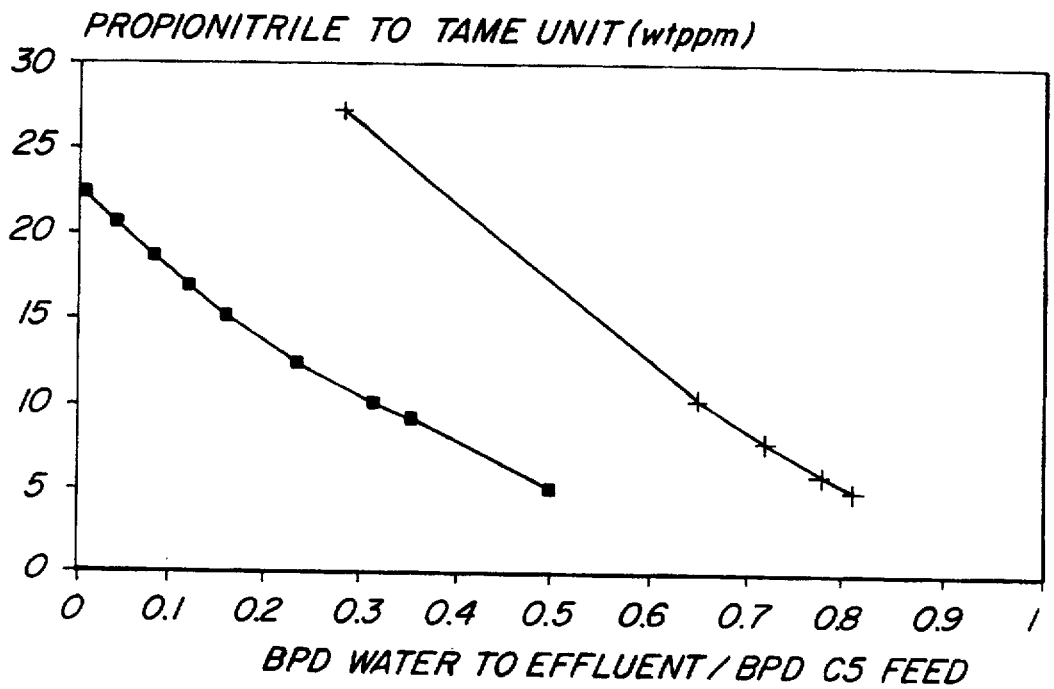
FIG. 3 is a chart illustrating the savings in the water employed to scrub nitriles from an etherification feedstock, initially comprising about 50 ppm-wt. propionitrile according to the process of the instant invention.

An engineering simulation of a water wash column treating a $C_5$ hydrocarbon feedstream to an etherification zone for the production of tertiary amyl methyl ether (TAME), FIG. 3, illustrates the required water wash rate relative to the feedstream rate on a volumetric basis to produce a treated hydrocarbon feedstream depleted in nitriles with an initial propionitrile concentration of about 50 ppm-wt. Operating lines are shown for a once-through water wash operation (+) and a water regeneration scheme of the instant invention (■). According to FIG. 3, to provide a treated feedstream with about 5 ppm of propionitrile, the once-through water wash operation required a wash water rate equal to over 80% of the feed rate, while the recycle scheme of the instant invention only required a wash water rate of less than 50% of feed rate or about 38% savings over the once-through operation.

EXAMPLE 2

Figure 4:
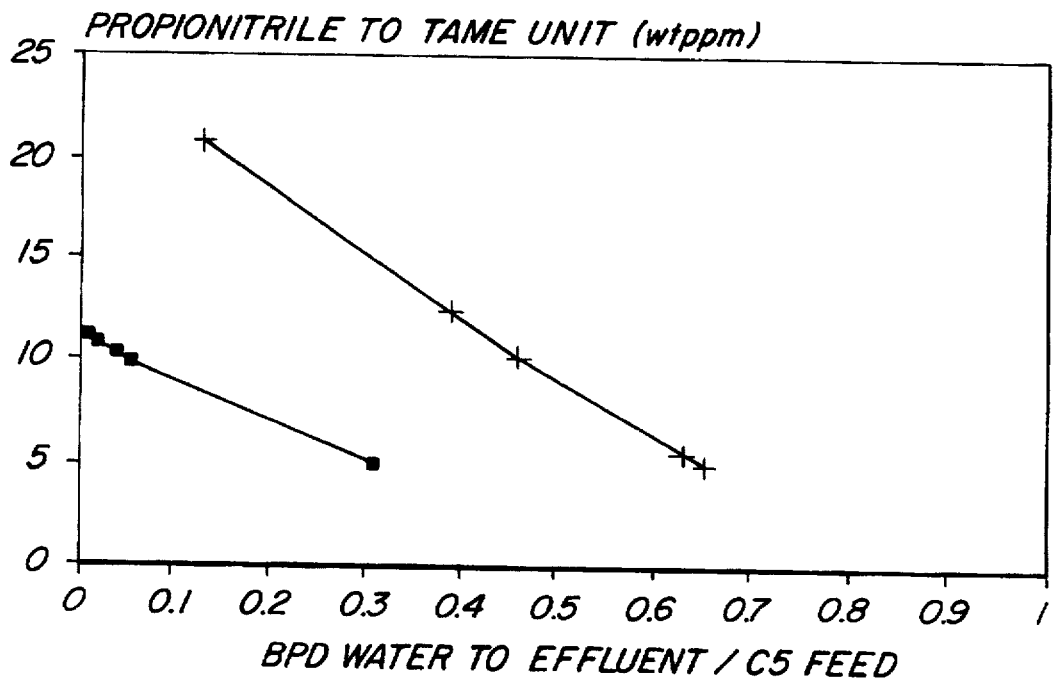
FIG. 4 is a chart illustrating the savings in water employed to remove nitriles from an etherification feedstock initially comprising about 25 ppm-wt propionitrile.

FIG. 4 illustrates the water wash rates relative to the feedstream to the etherification reaction zone of Example I when the feedstream comprises about 25 ppm-wt propionitrile. The operating lines in FIG. 4, as in FIG. 3, are shown for a once-through water wash operation (+) and a water regeneration scheme of the instant invention (■). According to FIG. 4, to reduce the propionitrile in the treated etherification zone feed to a level of 10 ppm propionitrile, the once-through scheme required a water wash rate of about 5% of the feed rate, while a once-through scheme required a water wash rate of about 46% of the feed rate. The difference between the once-through scheme and the water recirculation represents a savings of about 89% over the once-through operation for the water recirculation scheme of the present invention. Thus, the lower the concentration of propionitrile in the feedstream, the greater the savings with the water regeneration scheme of the instant invention.

We claim:

1. A process for the removal of nitriles including acetonitrile, propionitrile and mixtures thereof from an etherification zone feedstream comprising $C_4$–$C_6$ hydrocarbons and said nitriles, said process comprising:

a) passing said feedstream at water wash conditions including a water wash temperature to a water wash zone and contacting therein said feedstream with a regenerated water stream to provide a hydrocarbon feedstream depleted in said nitriles and spent water stream enriched in said nitriles relative to said regenerated water stream;

b) passing at least a portion of said spent water stream at water regeneration conditions including a water regeneration temperature to a water regeneration zone and contacting therein a nitrile-lean stream to absorb at least a portion of said nitriles from the spent water stream and to provide a nitrile-rich raffinate stream and a nitrile-lean water stream; and c) admixing at least a portion of the nitrile-lean water stream with a make up water stream to provide the regenerated water stream and introducing said regenerated water to the water wash zone.

2. The process of claim 1 wherein the nitrile-lean stream is a raffinate stream comprising unreacted hydrocarbons from the etherification zone being withdrawn from the etherification zone.

3. The process of claim 2 further comprising admixing said hydrocarbon feedstream with an alcohol stream and passing said hydrocarbon feedstream to said etherification reaction zone to provide an ether product and the raffinate stream.

4. The process of claim 1 further comprising withdrawing at least a portion of said spent water stream from the process.

5. The process of claim 1 wherein said water wash temperature ranges from about 20° C. to about 300° C.

6. The process of claim 1 wherein the water regeneration temperature ranges from about 20° C. to about 300° C.

7. The process of claim 1 wherein the feedstream comprises from about 10 wt-ppm to about 500 wt-ppm nitriles.

8. The process of claim 1 wherein the hydrocarbon feedstream depleted in the nitriles comprises from about 0.1 ppm to about 50 ppm nitriles.

9. The process of claim 1 wherein the hydrocarbon feedstream depleted in the nitriles comprises less than about 25 ppm nitriles.

10. The process of claim 1 wherein the hydrocarbon feedstream depleted in nitriles comprises less than 5 ppm-wt propionitrile.

11. The process of claim 1 wherein the make up water stream of step (c) ranges from 0.1% to about 100% of said feedstream.

12. The process of claim 1 wherein the nitrile-lean stream is selected from the group consisting of $C_7$–$C_8$ alkylate, $C_5$–$C_7$ isomerate, polymer gasoline and mixtures thereof.

13. The process of claim 12 further comprising passing the raffinate stream to an alcohol removal zone prior to passing the raffinate stream to said water regeneration zone.

14. The process of claim 1 wherein the ether is selected from the group consisting of MTBE, TAME, ETBE, TAEE, and THME.

15. The process of claim 1 wherein the wash water zone and the water regeneration zone are combined in a single column having an upper section containing the water wash zone and a lower section containing the water regeneration zone, wherein the spent water stream is withdrawn from a lower portion of the wash water zone and passed to an upper portion of the water regeneration zone and the regenerated water stream is withdrawn from the bottom of the water regeneration zone and passed to a point in the upper portion of the wash water zone.

16. The process of claim 15 further comprising introducing at least a portion of the make up water stream to the water wash zone at a point above the point where the regenerated water stream is introduced.

17. The process of claim 16 wherein the make up water stream is introduced from about 1 to 5 trays above the point at which the regenerated water stream is introduced.

18. The process of claim 1 further comprising passing at least a portion of said nitrile-rich raffinate stream to gasoline blending.

* * * * *